US008356764B2

(12) United States Patent
Aizenberg et al.

(10) Patent No.: US 8,356,764 B2
(45) Date of Patent: Jan. 22, 2013

(54) CONTINUOUS FLOW MICRO-CRUSHER

(75) Inventors: Joanna Aizenberg, New Providence, NJ (US); Thomas Krupenkin, Warren, NJ (US); Paul Kolodner, Hoboken, NJ (US); Joseph Ashley Taylor, Springfield, NJ (US)

(73) Assignee: Alcatel Lucent, Paris (FR)

( * ) Notice: Subject to any disclaimer, the term of this patent is extended or adjusted under 35 U.S.C. 154(b) by 1898 days.

(21) Appl. No.: 11/172,319

(22) Filed: Jun. 30, 2005

(65) Prior Publication Data
US 2007/0001045 A1 Jan. 4, 2007

(51) Int. Cl.
*B02B 1/00* (2006.01)
*B02C 11/08* (2006.01)
(52) U.S. Cl. ............................ 241/57; 241/100; 241/236
(58) Field of Classification Search .................. 241/236, 241/57, 46.06, 100
See application file for complete search history.

(56) References Cited

U.S. PATENT DOCUMENTS

| | | | | |
|---|---|---|---|---|
| 3,491,956 A * | 1/1970 | Barbod et al. | ................... | 241/57 |
| 3,529,777 A * | 9/1970 | Dodson et al. | ................... | 241/18 |
| 3,633,831 A * | 1/1972 | Dodson et al. | ................... | 241/61 |
| 3,862,721 A * | 1/1975 | Flair | ............................. | 241/236 |
| 4,359,193 A * | 11/1982 | Schonert | ........................... | 241/3 |
| 4,690,340 A * | 9/1987 | Hatanaka | ...................... | 241/236 |
| 5,169,078 A * | 12/1992 | Lamar | .......................... | 241/222 |
| 5,292,078 A * | 3/1994 | Lodovico et al. | ............. | 241/167 |
| 6,402,070 B1 * | 6/2002 | Ishida et al. | ................... | 241/236 |
| 6,755,365 B1 * | 6/2004 | Meredith | ........................ | 241/29 |
| 2002/0074438 A1 * | 6/2002 | Horigane | ...................... | 241/236 |

* cited by examiner

*Primary Examiner* — Bena Miller
(74) *Attorney, Agent, or Firm* — Hitt Gaines, PC

(57) ABSTRACT

The present invention provides an apparatus comprising a substrate and first and second disks. The disks are rotatably located over the substrate, each disk having an outer circumference with teeth thereon. The first disk is positioned to interleave one or more of its teeth with the teeth of the second disk. The substrate includes a channel with an exit port located near the teeth of one of the disks. Another apparatus comprises at least one disk rotatably located over a substrate and in a well of the substrate, the disk having an outer circumference with teeth thereon. The disk is positioned to provide a maximum distance of less than about 10 microns between each one the teeth and a nearest wall defining the well. The substrate includes a channel with an exit port located near the teeth of the disk.

18 Claims, 14 Drawing Sheets

CONTINUOUS FLOW MICRO-CRUSHER

TECHNICAL FIELD OF THE INVENTION

The present invention is directed, in general, to an apparatus and methods for breaking particles.

BACKGROUND OF THE INVENTION

In many biological applications, it is desirable to crush particles so that their contents can be analyzed. For instance, there is great interest in the development of cost-effective and rapid methods for analyzing particles comprising bacterial or other cells in military, medical, agricultural and food-preparation applications. For certain particle types, however, particle breaking, lysing or crushing is problematic.

For instance, when stressed or starved for nutrients, vegetative bacterial cells can differentiate into dormant endospores, more commonly referred to as spores. Spores are highly resistant to inactivation and rupture by various physical treatments, including mechanical crushing, ultraviolet and gamma radiation, heat, and chemical treatments.

Embodiments of the present invention overcome these problems by providing an apparatus to facilitate the crushing of particles, as well as methods of using and making such an apparatus.

SUMMARY OF THE INVENTION

To address the above-discussed deficiencies, one embodiment of the present invention is an apparatus. The apparatus comprises a substrate and first and second disks rotatably located over the substrate. Each disk has an outer circumference with teeth thereon. The first disk is positioned to interleave one or more of its teeth with the teeth of the second disk. The substrate includes a channel with an exit port located near the teeth of at least one of the disks. A maximum distance between adjacent ones of interleaved teeth is less than about 10 microns.

Another embodiment is an apparatus comprising a substrate and at least one disk rotatably located over the substrate and in a well of the substrate. The disk has an outer circumference with teeth thereon. The disk is positioned to provide a maximum distance of less than about 10 microns between each one the teeth and a nearest wall defining the well. The substrate includes a channel with an exit port located near the teeth of the disk.

Yet another embodiment is a method. The method comprises forming a channel in a substrate, the channel having an exit port. At least one disk is formed over the substrate and in a well of the substrate. The disk is rotatable and has an outer circumference with teeth thereon, the teeth being near the exit port.

BRIEF DESCRIPTION OF THE DRAWINGS

The invention is best understood from the following detailed description, when read with the accompanying FIGUREs. Various features may not be drawn to scale and may be arbitrarily increased or reduced in size for clarity of discussion. Reference is now made to the following descriptions taken in conjunction with the accompanying drawings, in which.

DETAILED DESCRIPTION

The present invention benefit from investigations that lead to a new understanding of the difficulties in mechanically crushing microparticles suspended in a liquid environment. It is difficult to crush microparticles because forces from the flowing liquid can move the microparticles away as the crushing components of a mechanical crusher are brought together. Embodiments of the present invention eliminate this problem by providing a continuous flow of microparticles to rotating crushing components.

Figure 1:
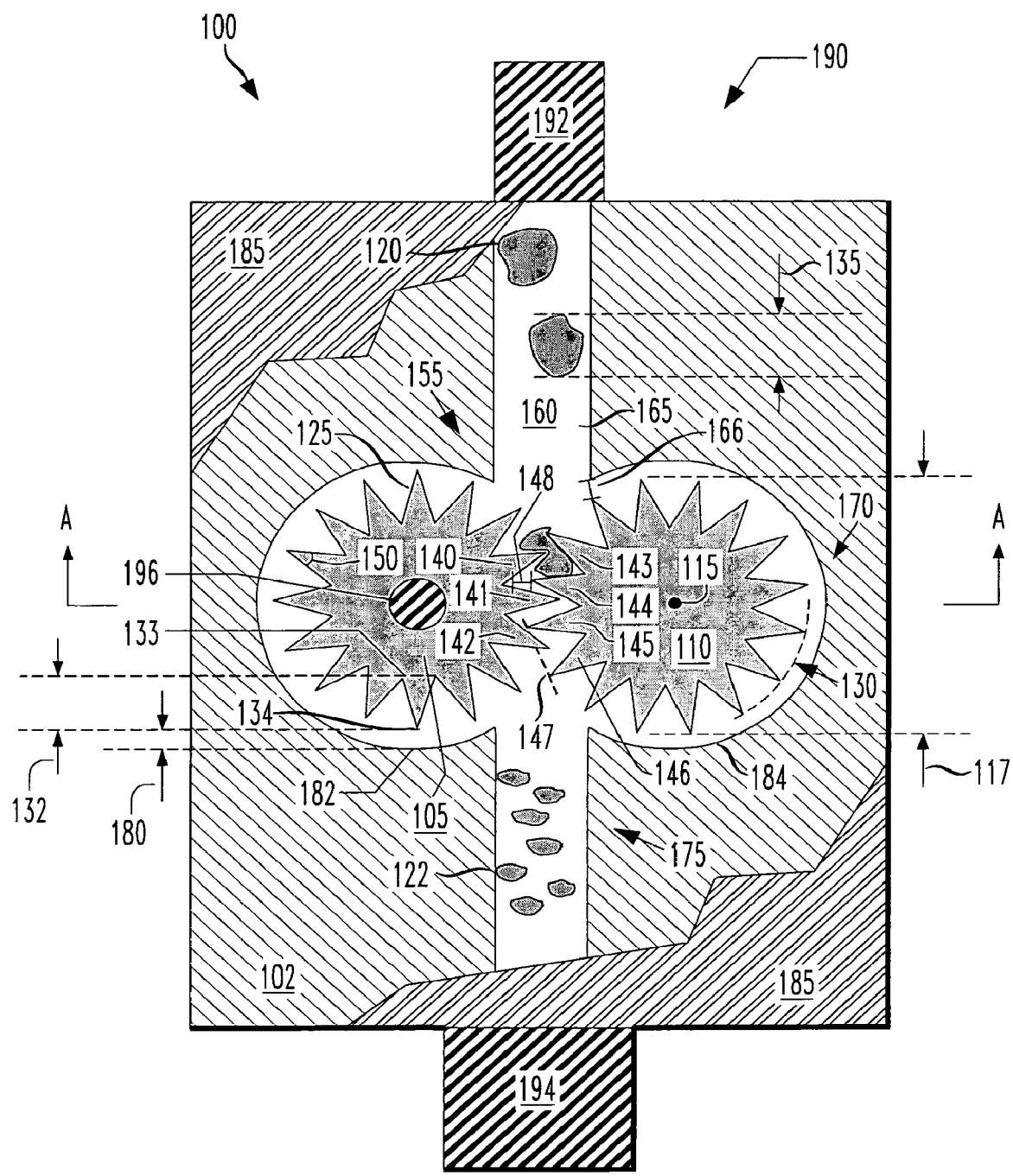
FIG. 1 illustrates a plan view of one embodiment of the apparatus having two disks.

One embodiment of the present invention is an apparatus. FIG. 1 illustrates a plan view of one embodiment of an apparatus 100. The apparatus 100 comprises a substrate 102 and first and second disks 105, 110. The disks 105, 110 are rotatably located over the substrate 102. Some preferred embodiments of the disks 105, 110 have outer dimensions of less than about 2000 microns. For instance, the disks 105, 110 can have diameters 117 and a vertical dimension (into and out of the plan of view depicted in FIG. 1) of about 2000 microns or less and in some cases about 1000 microns or less.

Embodiments of the substrate 102 and disks 105, 110 can comprise any material suitable for being formed into the components of the apparatus 100. Some preferred embodiments of the substrate 102 comprise a material that is hard enough to crush a microparticle 120. Such embodiments are advantageous in cases where the disks 105, 110 are formed from the substrate 102. In some cases the substrate 102 is a planar substrate, and more preferably, a stack of planar substrates that are in contact with each other. For instance, the substrate 102 can comprise an inorganic semiconductor, such as silicon or silicon-on-insulator (SOI). The disks 105, 110 can comprise the same or different material as the substrate 102. For example, the disks 105, 110 can comprise silicon. In other instances, either or both of the substrate 102 and disks 105, 110 comprise other materials such as plastics or metals.

Exemplary microparticles 120 have outer dimensions that are less than about 100 microns. The microparticle 120 can comprise biological cells, including plant, animal or bacterial cells. In some cases, the microparticle 120 is a bacterial spore, such as *Bacillus anthracis, subtilis,* or *thuringiensis.* The microparticle 120 can also comprise a nonbiological particle, such as a microsphere. Some preferred microspheres comprise a latex sphere holding chemicals inside the sphere.

Rotatable disks 105, 110 are desirable because they facilitate crushing of the microparticles 120 and can be easily used in embodiments that comprise a continuous-flow apparatus. Using the rotating disks 105, 110 in cooperation with a continuous flow of microparticles 120 towards the disks 105, 110 help to prevent the microparticles 120 from escaping the teeth 125 of the disks 105, 110, without being crushed. Minimizing the escape of non-crushed microparticles 120 increases yields of crushed microparticles 122 that can be processed in a given unit of time.

Each disk 105, 110 has an outer circumference 130 with teeth 125 thereon. Preferred embodiments of the disks 105, 110 are flat, have a circular circumference 130, and the disks 105, 110 are configured to rotate about an axis 115. Preferred embodiments of the teeth 125 form an array of protruding structures and in some cases a regular array of protruding structures. In some exemplary embodiments each of the teeth 125 have a length 132 from its base 133 to apex 134 that is about 5 times smaller than the diameter 117 of the disk 105. In some preferred embodiments the length 132 is less than the diameter 135 of the microparticle 120. Consider when the microparticle 120 has a diameter 135 of about 1 to about 1.5 microns as in a bacterial spore. In such instances, it is preferable for the tooth's length 132 to range from about 1 to 1.5 microns. In other preferred embodiments the tooth's length 132 is less than about 10 microns. In some cases it is desirable for the teeth 125 to comprise a triangular or pyramidal shape because this shape facilitates the conformal interleaving of teeth 125 from separate disks 105, 110, and crushing of the microparticles 120.

Crushing the microparticle 120 is facilitated by interleaving the teeth 125 located on separate disks 105, 110 as the disks 105, 110 rotate. The term crush or crushing as used herein refers to the application of a mechanical force that is sufficient to break, lyse, rupture, puncture or otherwise open, or disrupt the integrity of the microparticle 120. As illustrated in FIG. 1, the first disk 105 is positioned to interleave one or more of its teeth 140, 141, 142 with the teeth 143, 144, 145, 146 of the second disk 110. When the tooth 142 of one disk 105 passes through a line 147 draw between the apexes of two adjacent teeth 145, 146 on the other disk 110, then teeth 142, 145, 146 are adjacent interleaved teeth. The rotation of the first and second disks 105, 110 cooperate to apply a mechanical force through interleaved teeth 140-146 to a microparticle 120 locatable between the teeth 140 of the first disk 105 and the teeth 142 of the second disk 110. In some cases for instance, the teeth 125 are configured to crush, which includes puncturing, a membrane of the microparticle 120.

It is preferable for a maximum distance 148 between adjacent interleaved teeth 140-146 on the separate disks 105, 110 to be less than about 10 microns. Providing a maximum distance 145 of 10 microns or less facilitates crushing and prevents the microparticle 120 from escaping between the disks 105, 110 without being crushed. In some cases it is preferable for the distance 148 to be less than a diameter 135 of the microparticle 120 locatable between the interleaved ones of teeth 140-146. Consider a situation where the apparatus 100 is configured to crush a microparticle 120, such as a bacterium, having a diameter 135 of about 1 to about 1.5 microns. In such instances it is advantageous for the interleaved teeth 140-146 from different disks 105, 110 to be separated by a maximum distance 148 of about 1.5 or less, or in some cases by about 1 micron or less. Of course the minimum distance between interleaved teeth can range from up to the maximum distance 148, to zero distance, such as in embodiments where the teeth 125 from different disks 105, 110 touch each other at some stage during the rotation of the disks 105, 110. In some cases, the minimum distance is the substantially same as the maximum distance 148. Such may be the case when the teeth 125 from different disks 105, 110 remain separated and do not touch.

To facilitate the interleaving of teeth 140-146 from separate disks 105, 110, it is preferable for the apex 134 of the teeth 125 to have an angle 150 of less than about 90 degrees, and more preferably less than about 45 degrees. Additionally, crushing is facilitated when such a sharp angle 150 at the apex 134 provides a small area of contact with the microparticle 120. A small area of contact promotes the development of sufficiently high stresses at an interface between the interleaved teeth 140-146 and the microparticle 120 to thereby crush the microparticle 120. Of course, in some embodiments of the apparatus 100, at any one time more than one microparticle 120 can be located at the interface.

As further illustrated in FIG. 1, the substrate 102 includes a channel 155. In some cases, the channel 155 is located in the substrate 102 and its dimensions are configured to accommodate microparticles 120 and a fluid 160. The channel 155 also comprises an exit port 165 located near the teeth 125 of at least one of the disks 105, 110. In some cases, for example, the distance 166 between the exit port and circular circumference 130 is less than about 1000 microns and more preferably less than about 100 microns, and even more preferably less than about 10 microns. Having the exit port 165 near the teeth 125 facilitates crushing of the microparticle 120 and, in some cases, helps to prevent the microparticles from escaping the interleaved teeth 140-146.

The flow of fluid 160 through the channel 155 facilitates passage of the microparticles 120 through the channel 155 to the exit port 165 and to the disks 105, 110. Some preferred embodiments of the fluid 160 comprise water or other liquid suitable for forming a colloidal suspension of the microparticles 120. The fluid 160 can further include chemically or physically reactive substances such as a detergent or denaturant, or other liquids to facilitate the de-aggregation and fluid transport of the microparticles 120 through the channel 155.

It is advantageous to configure the channel 155 and the fluid 160 to carry the microparticles 120 to the disks 105, 110. In preferred embodiments the exit port 165 of the channel 155 is positioned to continuously deliver a flow of fluid 160, microparticles 120, or both, to the interleaved teeth 140-146 of the disks 105, 110. In some cases the disks 105, 110 are positioned such that the rotational motion of the disks 105, 110 is able to pump the fluid 160 from the channel 155. In other cases, the disks 105, 110 are positioned so that the movement of the fluid 160 through the channel 155 causes the rotational motion of the disks 105, 110.

As further illustrated in FIG. 1, in some preferred embodiments of the apparatus 100, the substrate 102 further includes one or more well 170 formed therein. The well 170 is configured to hold the interleaved teeth 140-146 of the disks 105, 110 near the exit port 165 as the disks 105, 110 rotate. In some cases the wells 170 fluidly couples the channel 155 to an effluent channel 175. Preferably the effluent channel 175 is formed in the substrate 102 and is configured to transport the fluid 160 and crushed microparticles 122 away from the disks 105, 110.

It is preferable for a maximum distance 180 between the apex 134 of the teeth 125 and the nearest of the walls 182, 184 defining the well 170 to be less than about 10 microns. Analogous to the above-discussion concerning the maximum distance 145 between interleaved teeth 140-146, it is preferable for the maximum distance 180 to be less than a diameter 135 of the microparticle 120 locatable between the teeth 125 and wall 182, 184. For example in some preferred embodiments, the maximum distance 180 is less than about 1.5 microns and, in some cases, less than about 1 micron.

So limiting the maximum distance 180 can facilitate crushing of the microparticle 120 between the wall 182, 184 and teeth 125. Additionally, limiting the maximum distance 180 helps to prevent the microparticle 120 from escaping between the teeth 125 and the walls 182, 184 without being crushed. In some cases limiting the maximum distance 180 as described above facilitates the movement of microparticles 120 into the interleaved teeth 140-146.

As also illustrated in FIG. 1, other advantageous embodiments of the apparatus 100 further include a second substrate 185. Preferably the second substrate 185 is located over the channel 155 and the disks 105, 110 and on the substrate 102. Only portions of the second substrate 185 are illustrated in FIG. 1 so that underlying structures can be depicted. It is desirable to configure the second substrate 185 to hold the disks 105, 110 in the well 170 and to hold the microparticles 120, fluid 160, or both, in the channel 155. The second substrate 185 can also be configured to hold the crushed microparticles 122 in the effluent channel 175. One skilled in the art would appreciate that various configurations of the substrate 102 and the second substrate 185 are possible. For instance, in some cases the second substrate 188 is a planar substrate. Both the substrate 102 and the second substrate 185 can be configured to comprise portions of structures such as the channel 155, well 170, and effluent channel 175. These structures are then completed by putting the two substrates 102, 185 together.

Advantageous embodiments of the apparatus 100 further comprise a continuous flow system 190. The continuous flow system 190 preferably includes a fluid delivery device 192 coupled to the channel 155 and a fluid collection device 194 coupled to the effluent channel 175. In some cases the fluid delivery device 192 comprises a pump or other hydraulic machine, configured to continuously pass microparticles 120, crushed microparticles 122 and material released therefrom, through the channel 155 and effluent channel 175. Some configurations of the fluid collection device 194 comprise instruments to analyze the crushed microparticles 122 or material released therefrom. Non-limiting examples of such instrumentation include machines to conduct immunological or nucleic acid assays, chromatographic and spectroscopic analysis, or combinations thereof. Some embodiments of the continuous flow system 190 further comprise a machine 196 configured to facilitate the rotation of the disks 105, 110. One of ordinary skill in the art would appreciate that there are numerous ways that the machine 196 can facilitate the rotation of the disks 105, 110.

Figure 2:
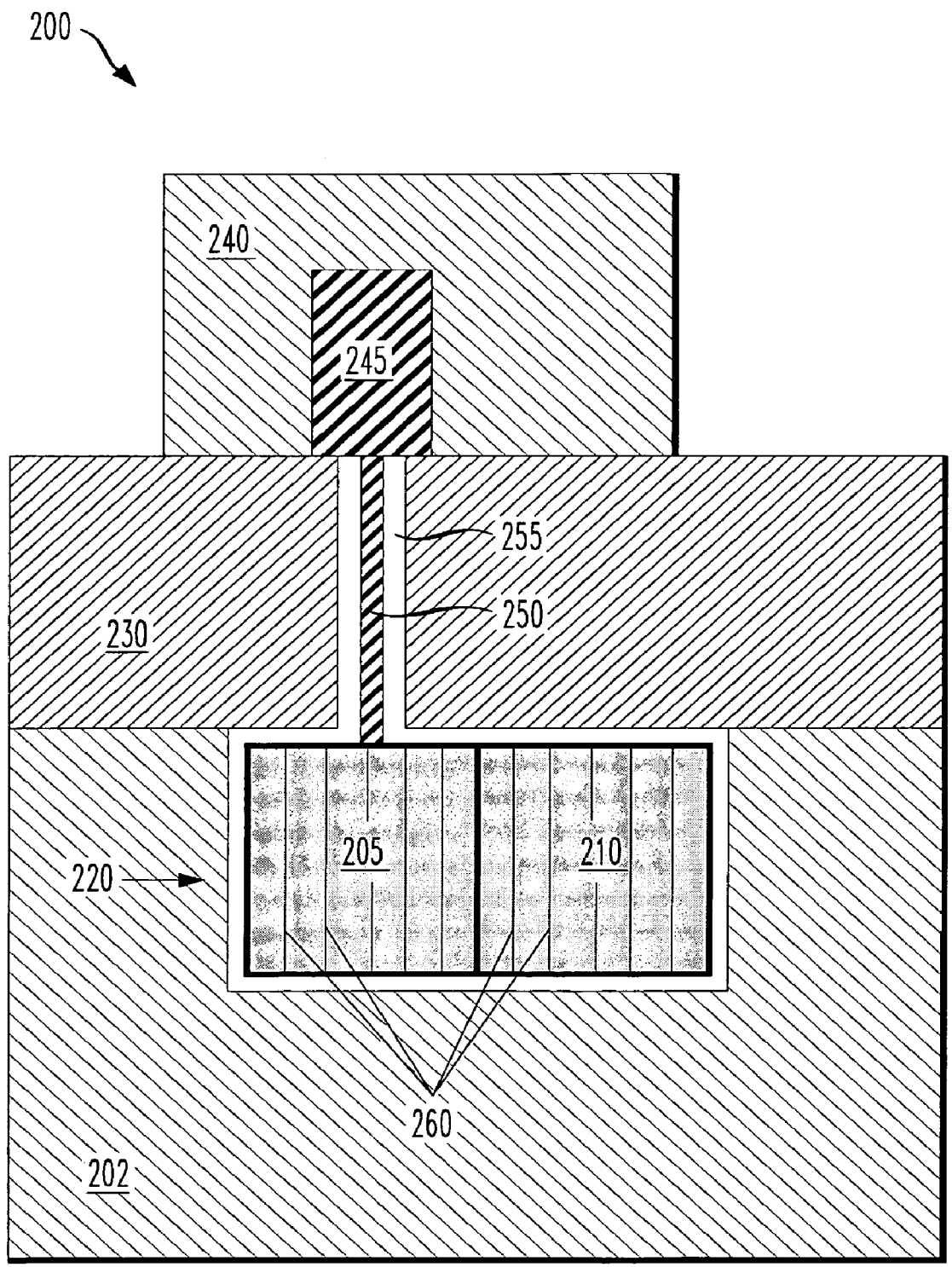
FIG. 2 illustrates a plan view of another embodiment of the apparatus mechanically coupled to a machine.
Figure 3:
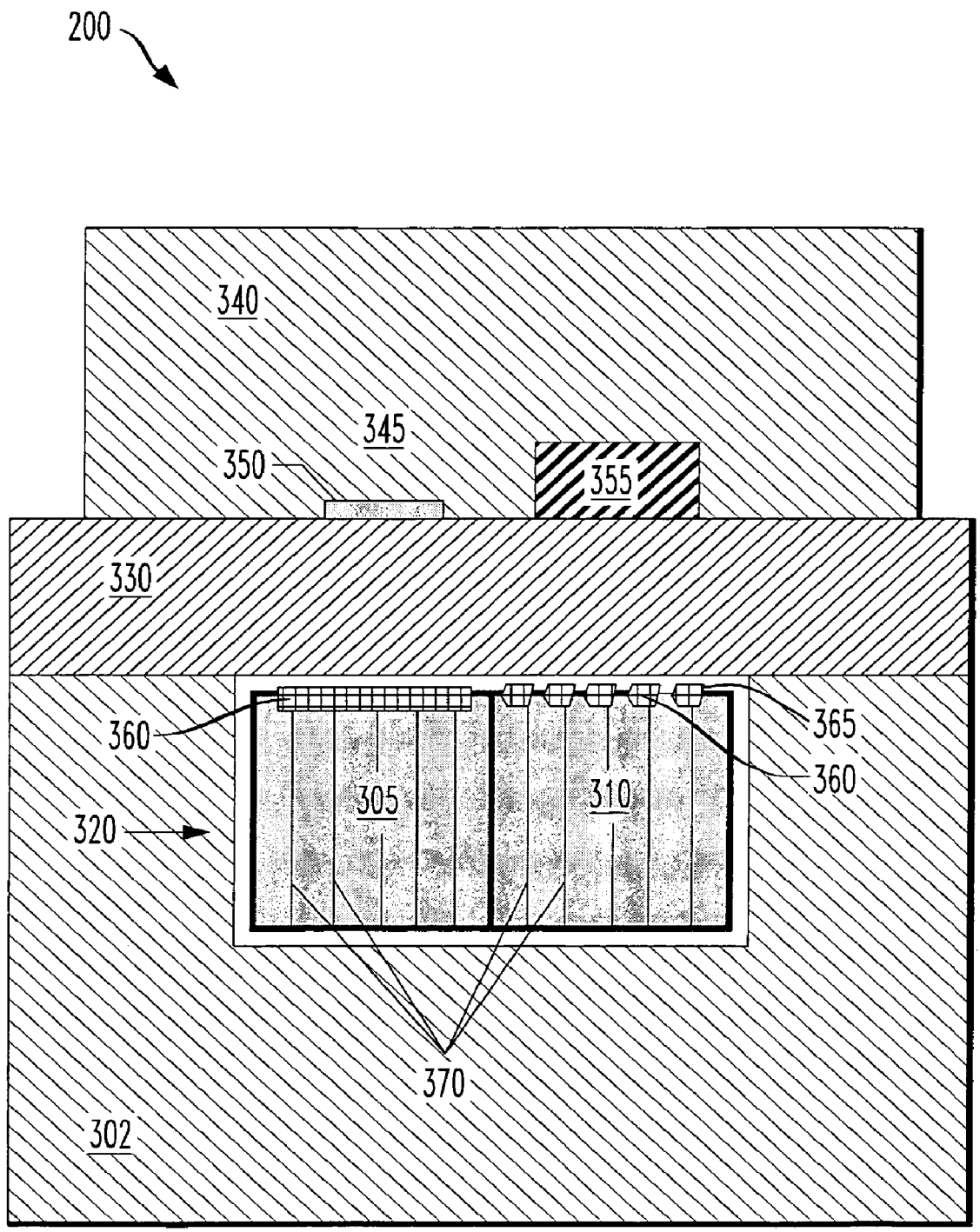
FIG. 3 illustrates a plan view of another embodiment of the apparatus magnetically coupled to a machine.
Figure 4:
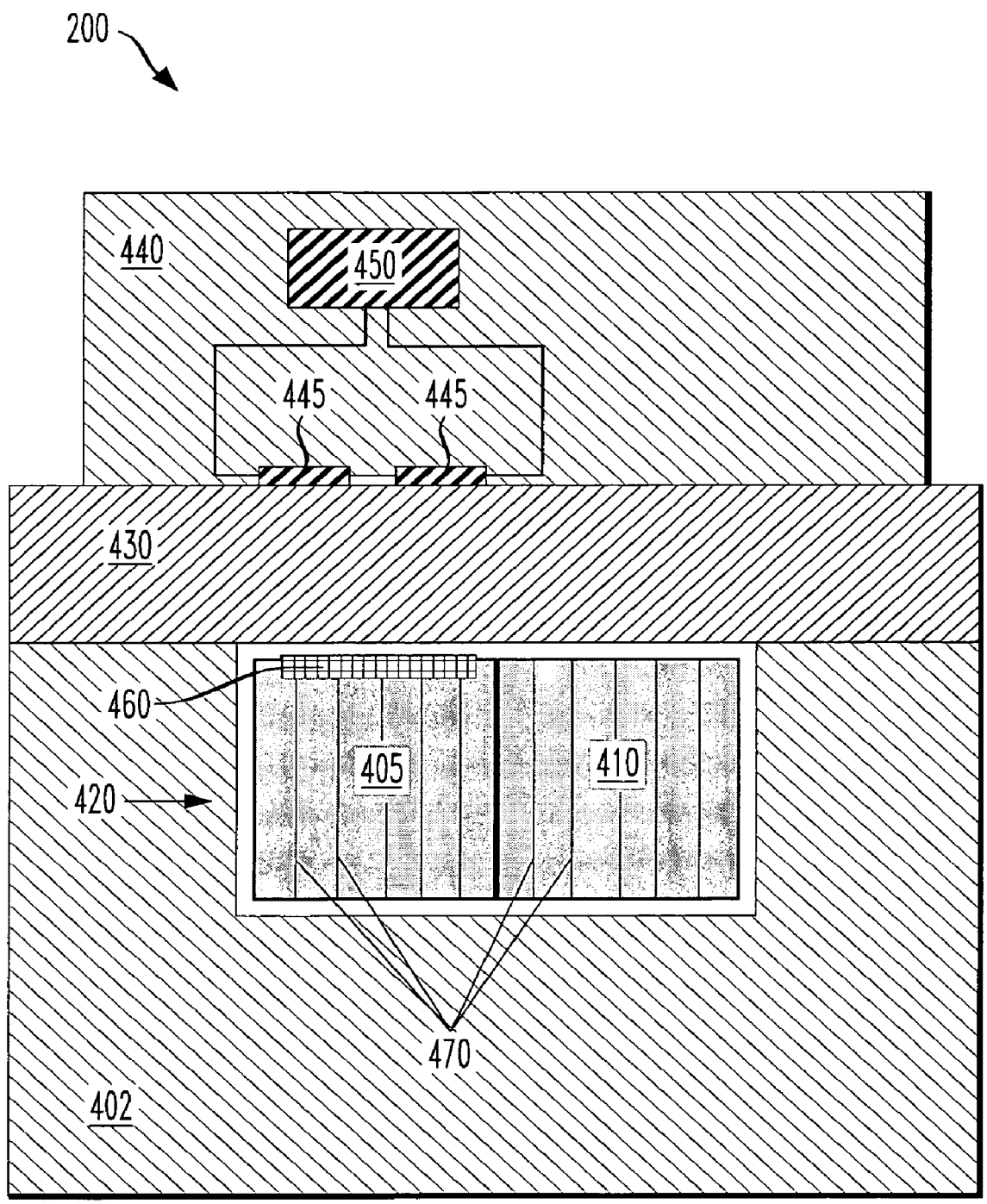
FIG. 4 illustrates a plan view of another embodiment of the apparatus electrostatically coupled to a machine.

FIGS. 2-4 present cross-sectional views, corresponding to view A-A in FIG. 1, of selected aspects of exemplary apparatuses to illustrate the different ways in which a machine can facilitate the rotation of the disks. In some cases, such as illustrated in FIG. 2, a machine mechanically coupled to the disks causes the disks to rotate.

The apparatus 200 illustrated in FIG. 2 comprises a substrate 202, first and second disks 205, 210, well 220, and a second substrate 230 positioned similar to that illustrated in FIG. 1. As illustrated in FIG. 2, the apparatus 200 also comprises a machine 240 located over the second substrate 230. The machine 240 is mechanically coupled to one or more of the disks 205, 210, thereby causing the disks 205, 210 to rotate. For the embodiment illustrated in FIG. 2, the machine 240 comprises a motor 245 that is mechanically coupled to the first disk 205. Mechanical coupling is via an axel 250 that passes through an opening 255 in the second substrate 230. Operating the machine 240 causes the motor 245 to rotate the axel 250, which in turn, rotates the disk 205. The teeth 260 of the first and second disks 205, 210 can interleave so that rotation of the first disk 205 causes the second disk 210 to also rotate.

In other cases, such as illustrated in FIG. 3, a machine magnetically coupled to the disks causes the disks to rotate. The apparatus 300 illustrated in FIG. 3 comprises a substrate 302, first and second disks 305, 310, well 320, and a second substrate 330 positioned similar to that illustrated in FIGS. 1 and 2. The apparatus 300 also comprises a machine 340 located over the second substrate 330. The machine 340 is magnetically coupled to one or more of the disks 305, 310.

In some cases, the machine 340 comprises a motor 345, which is coupled to a magnet 350. The magnet 350 can be a permanent magnet or an electromagnet. In other cases, the machine 340 comprises one or more stationary coils 355 configured to generate a rotating electromagnetic field when a current is passed through the stationary coils 355. At least one of the disks 305, 310 comprise a ferromagnetic material 360. For instance, the ferromagnetic material 360 can be in or on the disk 305. In some cases the ferromagnetic material 360 is enclosed in microspheres 365 that are chemically bonded to the surface of the disks 305, 310. One of ordinary skill would understand how to position the magnet 350 or stationary coils 355 near the disks 305, 310 to magnetically couple to the ferromagnetic material 360 of the disks 305, 310.

In some instances, operating the machine 340 causes the motor 345 to rotate the magnet 350. In other instances, operating the machine 340 causes the stationary coil 355 to generate a rotating electromagnetic field. The rotation of the magnet 350 or the rotating electromagnetic field causes at least one of the disks 305, 310 to rotate. Similar to that discussed above for FIG. 2, the teeth 370 of the first and second disks 305, 310 can interleave so that rotation of the disk 205, 310 coupled to the magnet 350 cause the other disk 305, 310 to also rotate.

In yet other cases, such as illustrated in FIG. 4, a machine electrostatically coupled to the disks causes the disks to rotate. The apparatus 400 illustrated in FIG. 4 comprises a substrate 402, first and second disks 405, 410, well 420, and a second substrate 430 positioned similar to that illustrated in FIGS. 1-3. The apparatus 400 also comprises a machine 440 located over the second substrate 430. The machine 440 is electrostatically coupled to one or more of the disks 405, 410.

In some cases, the machine 440 comprises a plurality of contact pads 445, which are individually connected to a voltage source 450. At least one of the disks also comprises one or more second contact pad 460. In some cases, the contact pads 445 and second contact pad 460 comprises a metal such as aluminum, gold or silver. One of ordinary skill would understand how to position the contact pads 445 near the disks 405, 410. One skilled in the art would also understand how to adjust the potential applied by the voltage source 450 to cause electrostatic coupling between the contact pads 445 and the second contact pad 460.

Operating the machine 440 comprises switching on the voltage source 450 to apply successive potentials to the contact pads 445 in a rotating sequence. The second contact pad 460 of the disks 405, 410 is kept at ground potential. The resulting electrostatic forces between the contact pads 445 and second contact pad 460 causes at least one of the disks 405, 410 to rotate. As discussed above, the teeth 470 of the first and second disks 405, 410 can interleave so that rotation of one disk 405, 410 by the machine 440 causes the other disk 405, 410 to also rotate.

Figure 5:
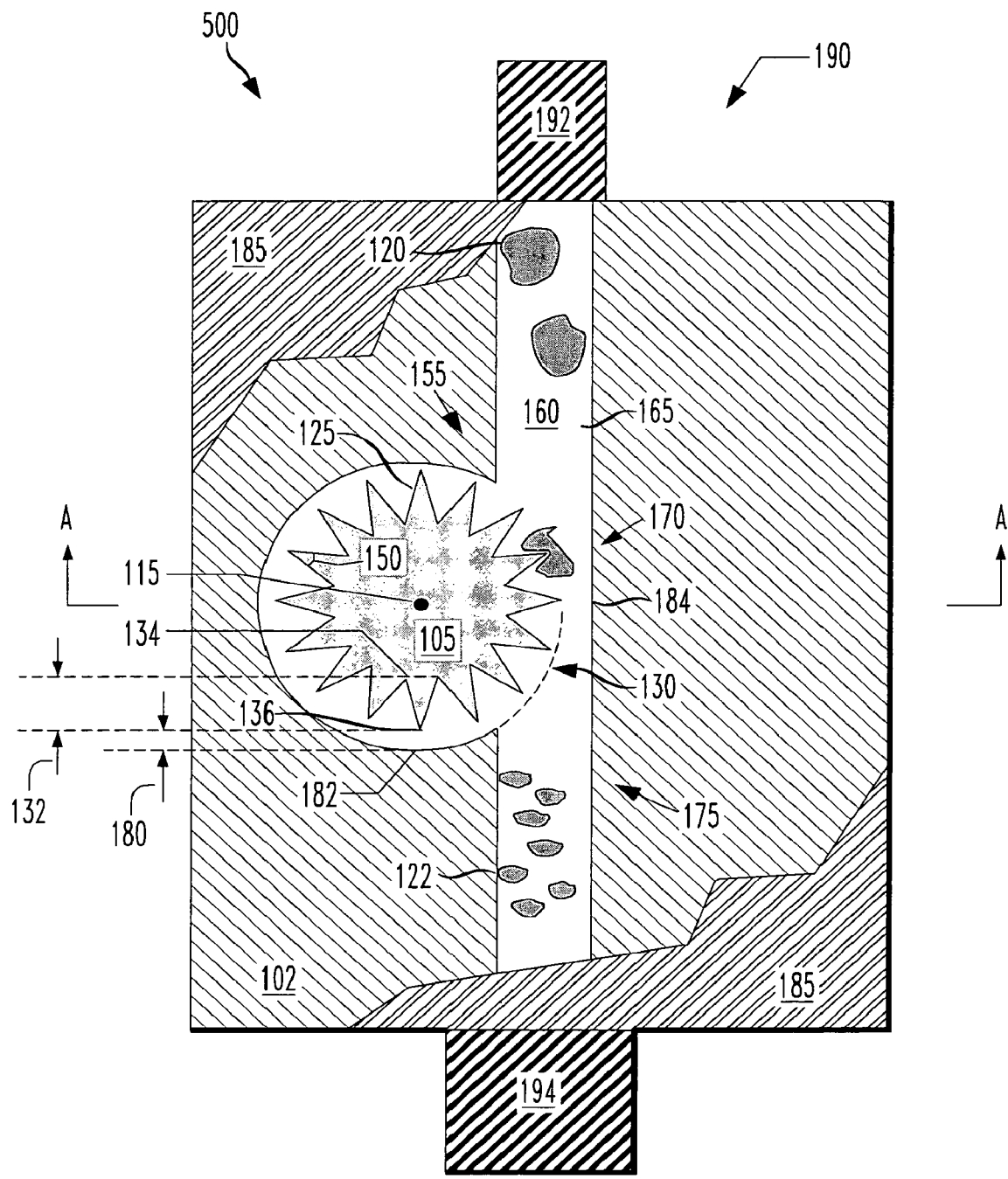
FIG. 5 illustrates a plan view of another embodiment of the apparatus having one disk.

Of course the apparatus have other than two disks. For example, FIG. 5 illustrates a plan view of an apparatus comprising at least one disk. Like reference numbers are used to identify components that are analogous the components of the apparatus shown in FIG. 1. The apparatus 500 can comprise a substrate 100 and at least one disk 105 rotatably located over the substrate 102. In some cases a single disk configuration such as shown in FIG. 5 is preferred because a smaller number of moving parts have to be constructed and then configured to operate in cooperation with each other.

As illustrated in FIG. 5, the disk 105 is located in a well 170 of the substrate 102. The disk has an outer circumference 130 with teeth 125 thereon. The teeth 125 are positioned to provide a maximum distance 180 of less than about 10 microns between each of the teeth 125 and a nearest portion of wall 182, 184 defining the well 170. The substrate 102 includes a channel 155 with an exit port 165 located near the teeth 125 of the disk 125. The apparatus 500 can comprise any embodiments of any of the components of the apparatuses described above and illustrated in FIGS. 1-4. For instance, the substrate 102 can be a planar substrate and the apparatus 500 can further comprise a second planar substrate 185 in contact with the planar substrate 102, with the disk 125 located therebetween. One of ordinary skill in the art will readily appreciate that other embodiments of the apparatus can have a plurality of disks configured as singles disks such as shown in FIG. 5 or configured as two more disks whose teeth interleave such as shown in FIG. 1. Of course some embodiments of the apparatus can have both configurations.

Figure 6:
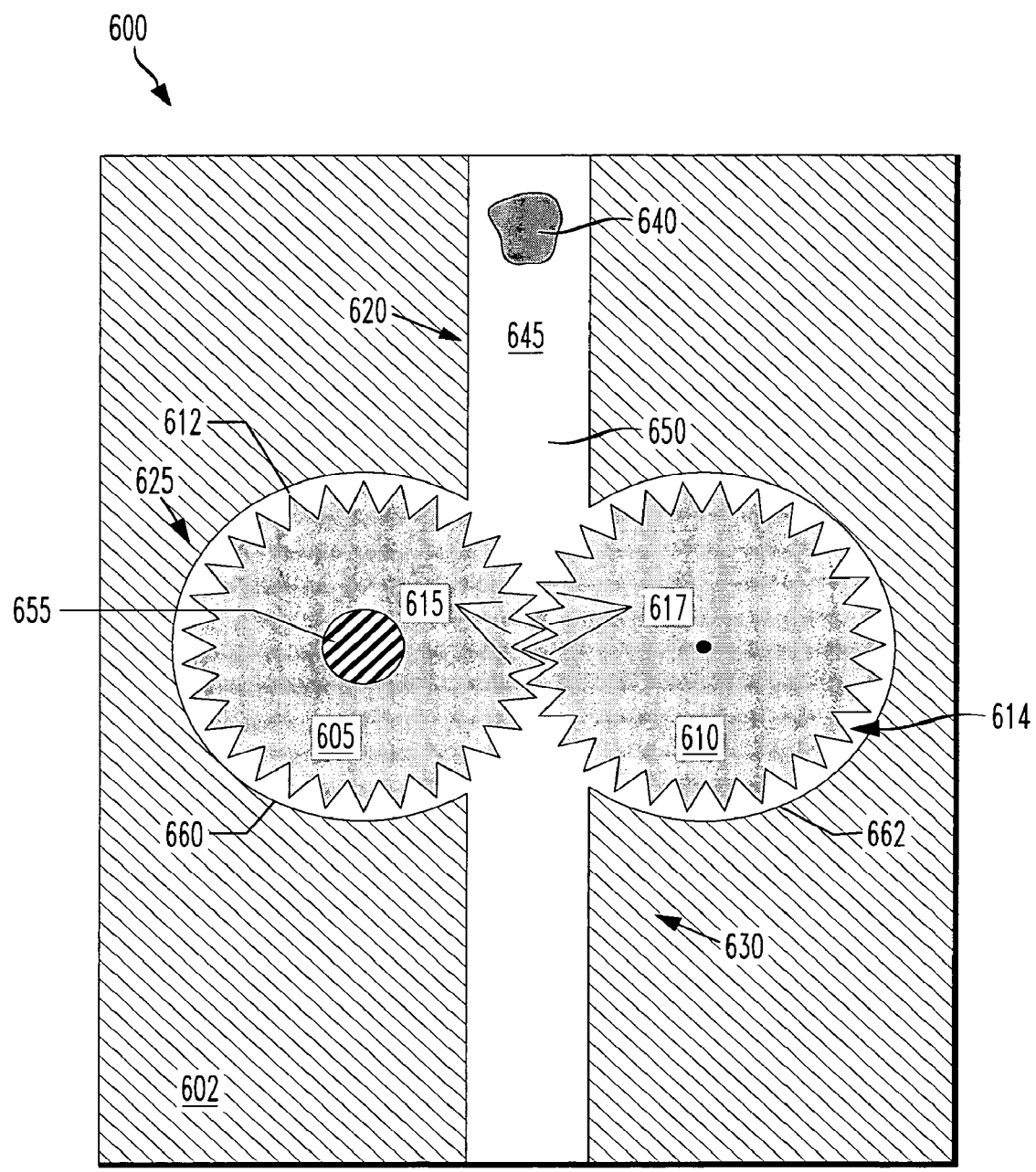
FIGS. 6-7 illustrate plan views of an exemplary apparatus at selected stages in a method of using the apparatus to crush a microparticle.
Figure 7:
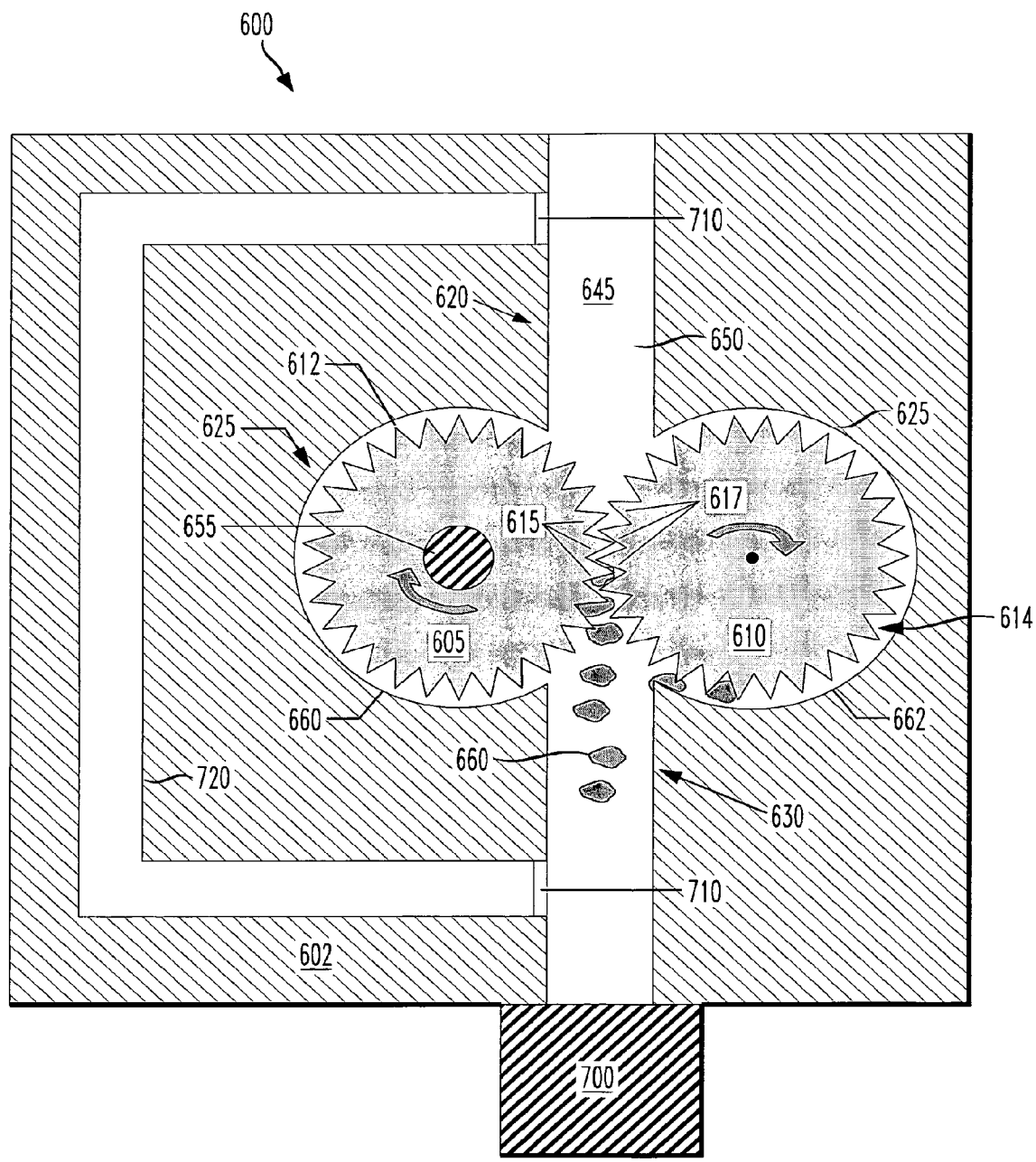

Another embodiment of the present invention is a method of use. FIGS. 6-7 illustrate plan views of an exemplary apparatus at selected stages in a method to crush a microparticle. Turning first to FIG. 6, the apparatus 600 can comprise any of the embodiments discussed above and shown in FIGS. 1-5. The apparatus 600 illustrated in FIG. 6 comprises a substrate 602. Using the apparatus 600 comprises rotating at least one disk, such as first and second disks 605, 610, located over the substrate 602. The disks 605, 610 have teethed 612 outer circumferences 614. In embodiments having at least two disks 605, 610, the disks 605, 610 are positioned to interleave a portion of their teeth 615, 617. Advantageous embodiments of the apparatus 600 further comprise a channel 620 located in the substrate 602, well 625, an effluent channel 630 and other components that can be configured analogous to that discussed and illustrated in FIGS. 1-4.

FIG. 6 further illustrates the apparatus 600 after placing a microparticle 640 in the apparatus 600. In some cases, the microparticle 640 is placed in the apparatus 600 by being introduced into a continuous flow of fluid 645 passing through the channel 620 and towards the disks 605, 610. In some cases the microparticle 640 is suspended in the fluid 645 before being introduced into the channel 620. The fluid 645 leaves an exit port 650 of the channel 620 and passes between the teeth 612 and one or more wall 660, 662 of the well 625 during the rotating of the disks 605, 610. In embodiments having at least two disks 605, 610 the fluid 645 leaves the exit port 650 and passes between the interleaved teeth 615, 617.

Any of the above-described embodiments of the apparatus discussed in the context of FIGS. 1-5 can be used to rotate the disks 605, 610. In some cases, the flow of fluid 645 through the channel 620 causes the disks 605, 610 to rotate. In other cases, rotating the disks 605, 610 causes the fluid 645 to be pumped from the channel 620. Some preferred embodiments of the apparatus 600 comprise a machine 655 to facilitate the rotation of one or more disks 605, 610. Preferably, the machine 655 is coupled to one or more of the disks 605, 610, thereby causing the disks 605, 610 to rotate. Coupling to the one or more disks 605, 610 can be mechanical, magnetic or electrostatic, such as discussed above in the context of FIGS. 2-4.

With continuing reference to FIG. 6, FIG. 7 illustrates the apparatus after rotating the disks 605, 610 to cause microparticles 640 shown in FIG. 6 to be crushed between the teethed 612 outer circumferences 614 of the disks 605, 610. In some cases the microparticles can be crushed between the teeth 612 and the walls 660, 662 of the well 662. In embodiments having at least two disks 605, 610, the microparticles 640 can be crushed between the interleaved ones of the teeth 615, 617 as the disks 605, 610 rotate. For the embodiment depicted, the crushed microparticles 660 and their contents are directed by the continuous flow of fluid 645 through the effluent channel 630.

In some cases, the effluent channel 630 is coupled to an instrument 700 that analyzes the crushed microparticles 660 and their contents. In other cases, the effluent channel 630 is coupled back into the channel 620, such that yet uncrushed or insufficiently crushed microparticles 640 are directed to the disks 605, 610 where they are crushed as described above. In some embodiments, a filter or valve 710 directs the microparticle 640 (shown in FIG. 6) or its crushed products 660 to the analytical instrument 700 or to a recycling channel 720. The recycling channel 720 couples the effluent channel 630 to the channel 620. Microparticles 640 can be recycled through the apparatus 600 as many times as necessary to maximize crushing before being directed elsewhere for analysis. Repeated cycling of microparticles 640 through the apparatus 600 is desirable in instances where the apparatus 600 is being used to crush microparticles 640 having a range of different sizes or hardness.

Yet another embodiment of the present invention is a method of manufacturing an apparatus. FIGS. 8-14 illustrate plan and cross-sectional views of selected stages in an exemplary method of manufacturing an apparatus 800. Any of the above-discussed embodiments of the apparatuses shown in FIG. 1-7 can be incorporated into the method of manufacture.

Figure 8:
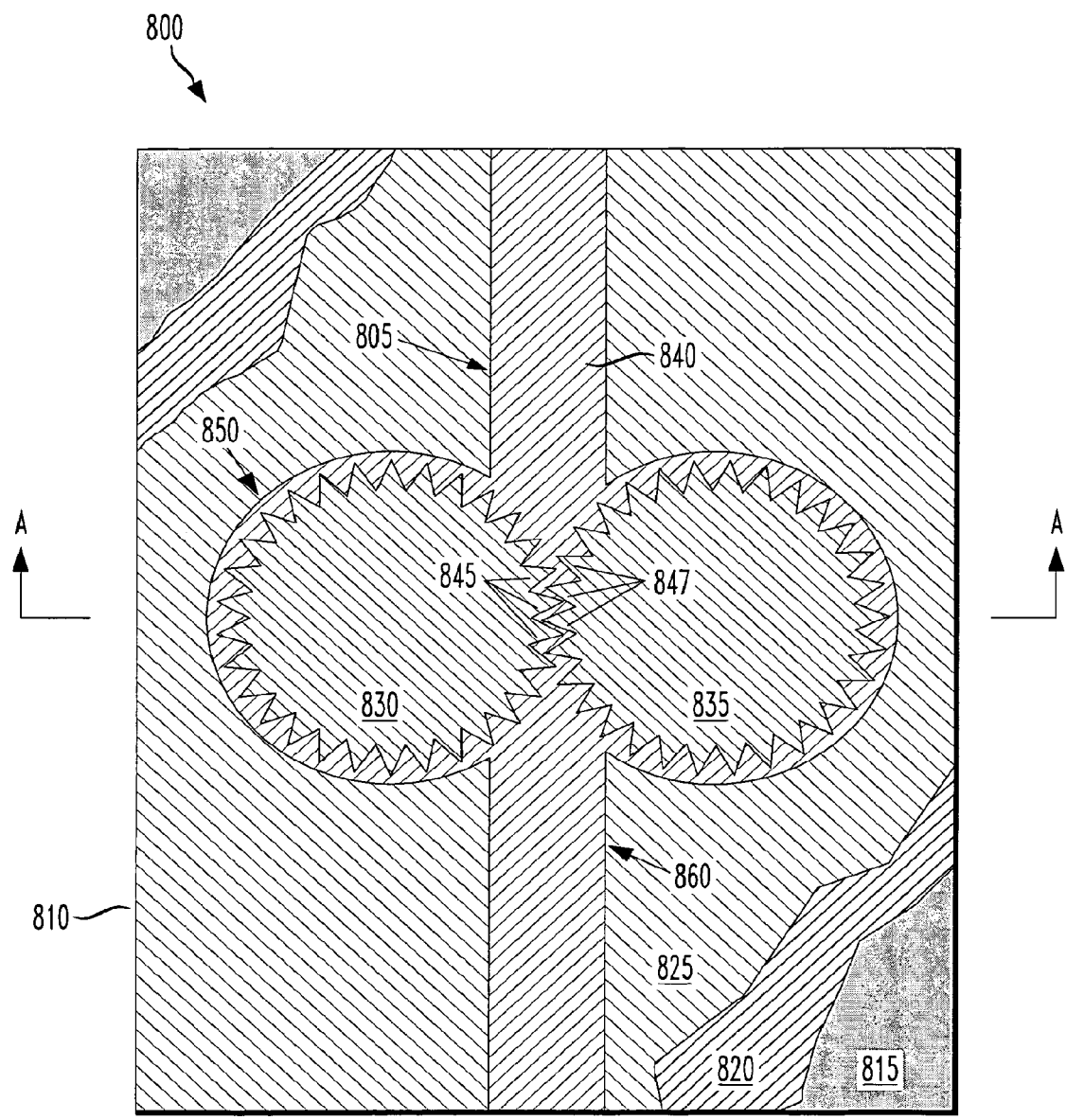
FIGS. 8-14 illustrate plan and cross-sectional views of selected stages in an exemplary method of manufacturing an apparatus.

Turning to FIG. 8, illustrated is the partially constructed apparatus 800 after forming a channel 805 in a substrate 810. In some preferred embodiments the substrate 810 is a planar semiconductor substrate, and more preferably, a silicon-on-insulator (SOI) wafer. The substrate 810 presented in FIG. 8 comprises a base silicon layer 815, a silicon dioxide layer 820 and top silicon layer 825. Portions of the silicon dioxide layer 820 and top silicon layer 825 are not shown so that underlying structures can be depicted.

The channel 805 is formed in the substrate 810 using conventional semiconductor patterning and dry etching procedures well known to those skilled in the art. In some preferred embodiments the channel 805 is etched out of the top silicon layer 825 and the silicon oxide layer 820 advantageously serves as an etch stop. Of course, in other embodiments, the substrate 810 can comprise a plurality of planar layers made of these or other types of conventional materials that are suitable for patterning and etching.

FIG. 8 also shows the apparatus 800 after forming at least one disk, such as first and second disks 830, 835, over the substrate 810 and near the exit port 840 of the channel 805. Preferably, the disks 830, 835 are etched out of the top silicon layer 816, and the silicon oxide layer 820 serves as an etch stop. It is advantageous for the disk or disks 830, 835 to be formed as part of the same patterning and dry etching steps used to form the channel 805. In embodiments where at least two disks are formed, one of the disks 830 is positioned to interleave one or more of its teeth 845 with the teeth 847 of the second disk 835. The teeth 845, 847 of at least one disk 830, 835 is near the exit port 840 of the channel 840.

As further illustrated in FIG. 8, it is desirable to form the disk or disks 830, 835 in a well 850 of the substrate 810. It is advantageous to form the well 850 in the substrate 810 as part of the same patterning and dry etching steps used to form the disks 830, 835. For the embodiment illustrated in FIG. 8, the well 850 is coupled to the exit port 840 of the channel 805. In certain embodiments of the method it also desirable to form an effluent channel 860 in the substrate 810 as part of the same patterning and dry etching steps used to form the channel 805 and disks 830, 835. For the embodiment illustrated in FIG. 8, the effluent channel 860 is coupled to the well 850.

Figure 9:
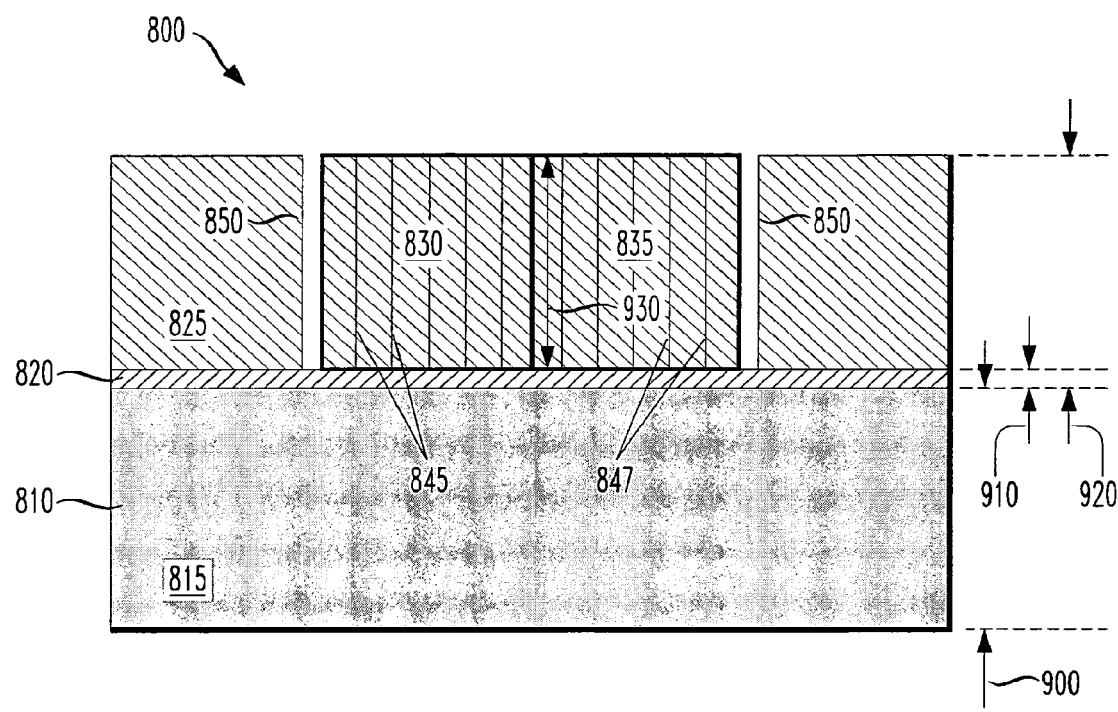

FIG. 9 presents a cross-sectional view, corresponding to view A-A in FIG. 8, of the partially constructed apparatus 800 at the same stage of manufacture as shown in FIG. 8. In some advantageous embodiments, the base silicon layer 815, the silicon dioxide layer 820 and top silicon layer 825 have thicknesses 900, 910, 920 of about 1100 to about 10000 microns, about 100 to about 200 microns, and about 1000 to about 10000 microns, respectively. In cases where the disks 830, 835 are etched out of the top silicon layer 825, the vertical dimension 930 of the disks 830, 835 are substantially the same or less than the thickness 920 of the top silicon layer 825. As further illustrated in FIG. 9 after dry etching, the disks 830, 835 remain attached to the substrate 810 via the silicon dioxide layer 820.

Figure 10:
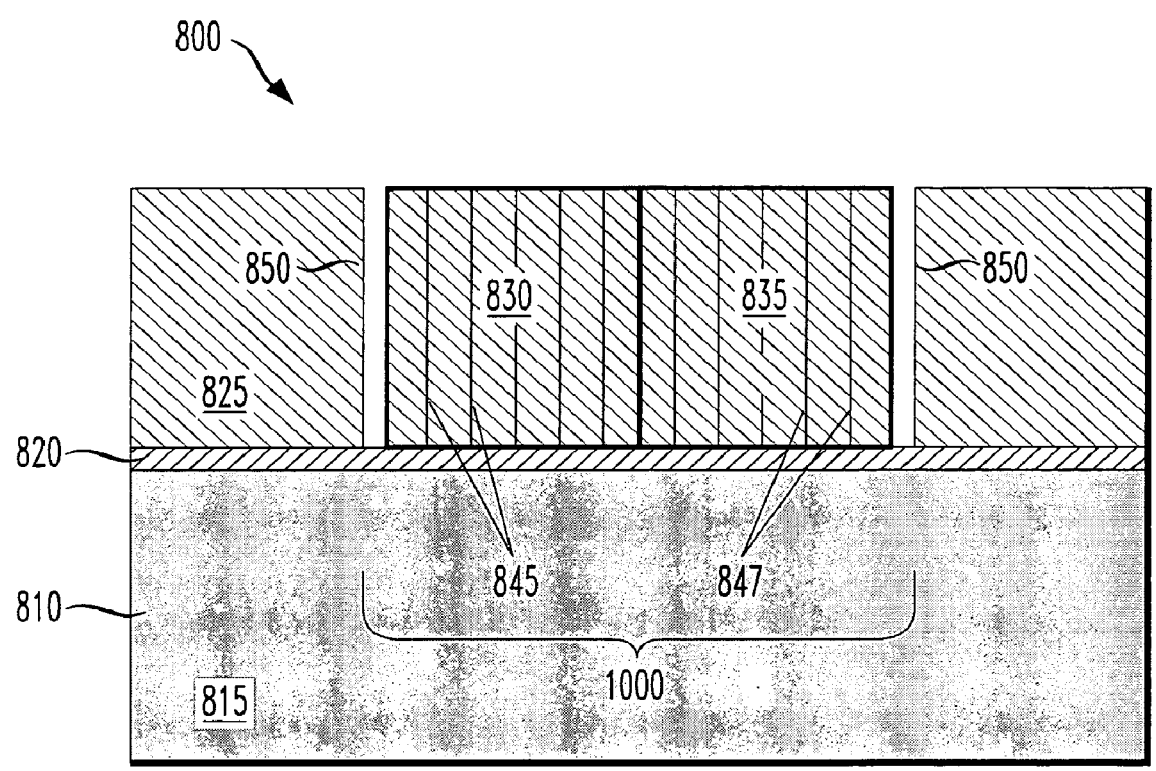

With continuing reference to FIGS. 8-9, FIG. 10 shows a cross-sectional view of the partially constructed apparatus 800 after releasing the disk or disks 830, 835 from the substrate 810. As illustrated in FIG. 10, the disks 830, 835 are released from the substrate 810 by removing at least those portions of the silicon dioxide layer 820 that are attached to the disks 830, 835. Conventional procedures, such as acid etching with hydrogen fluoride, are performed to remove the silicon dioxide layer 820 from a region 1000 underlying the disks 830, 835. As shown in FIG. 10, the released disks 830, 835 are over the substrate 810. The released disk or disks 830, 835 are rotatable because they are no longer physically connected to the substrate 810.

Figure 11:
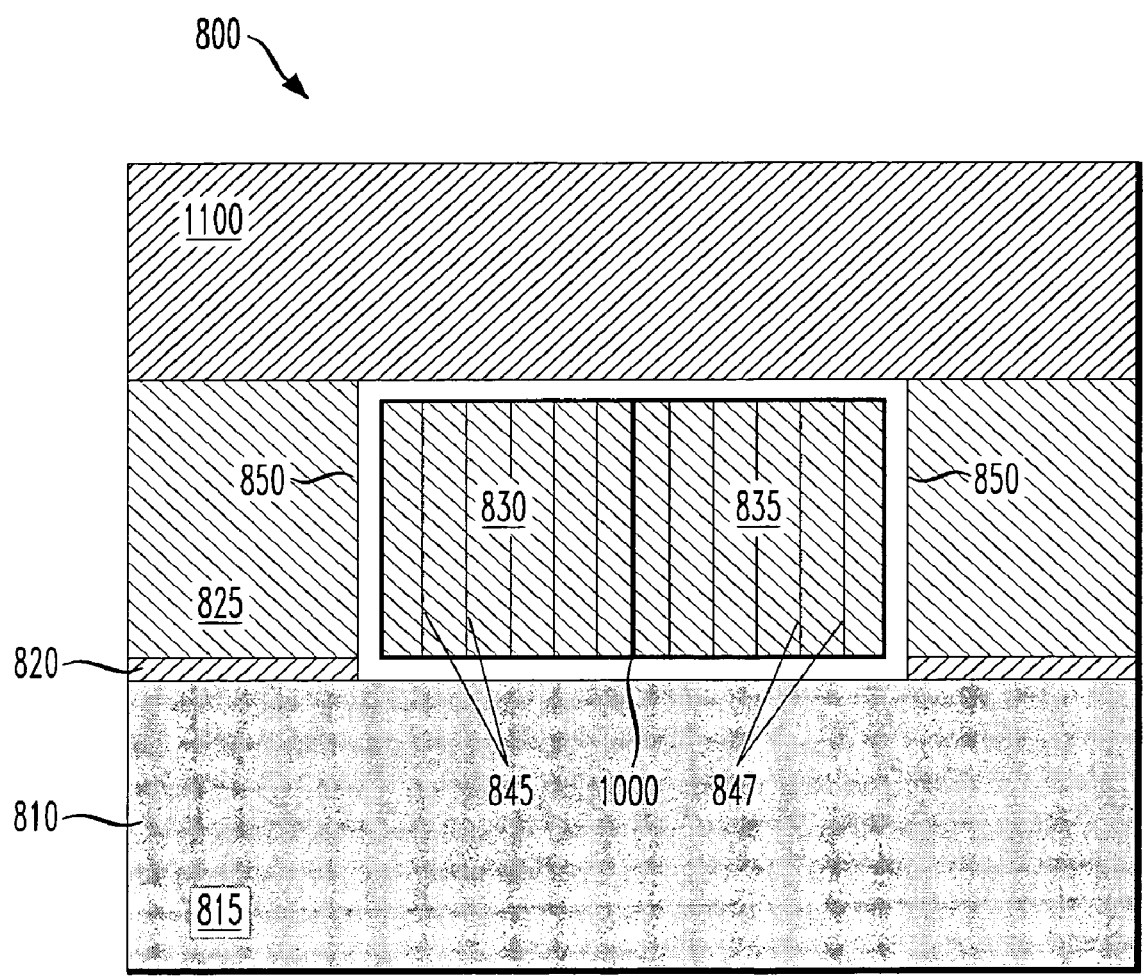

Referring now to FIG. 11, while maintaining reference to FIGS. 8-10, illustrated is a cross-sectional view of the partially-constructed apparatus 800 after coupling an optional second substrate 1100 to the substrate 810. The second substrate 1100 is located over the channel 805 and the disks 830, 835. The second substrate 1100 is configured to hold the at least one disk 830, 835 within the well 850. In some cases, the second substrate 1100 is also configured to hold microparticles and fluid in the channel 805, well 850, or effluent channel 860 (shown in FIG. 8).

To save money and time when the objective is to mass-produce multiple copies of the apparatus 800, it is sometimes desirable to use alternative materials and methods than discussed above. For instance, the component structures of the apparatus 800 can be separately mass-produced and then assembled. As an example the component structures of the apparatus 800 can be made similar to that presented in FIGS. 8-11 but not assembled. These component structures are then used as templates for casting molds and forming replicas of the component structures.

Figure 12:
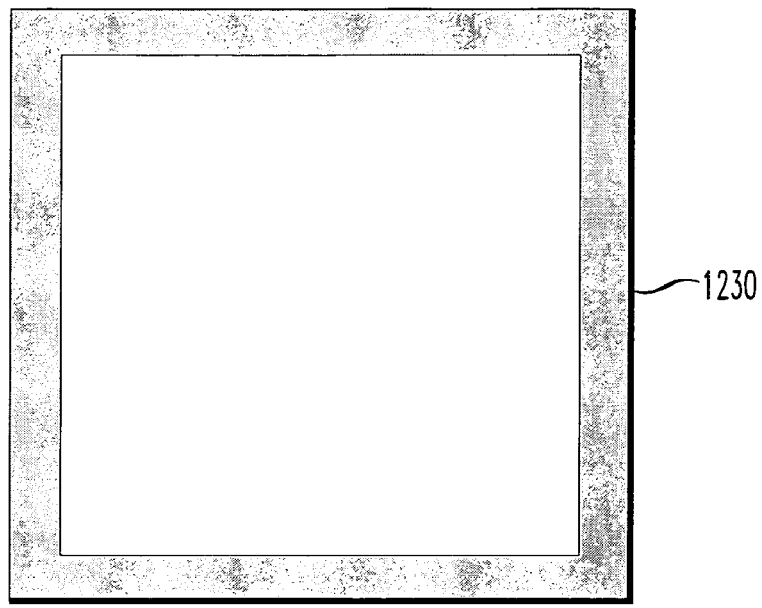
Figure 12:
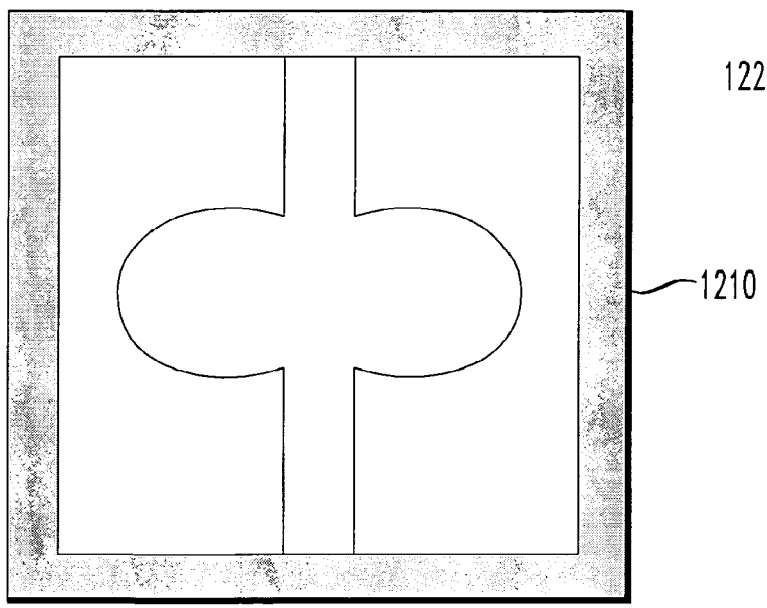
Figure 12:
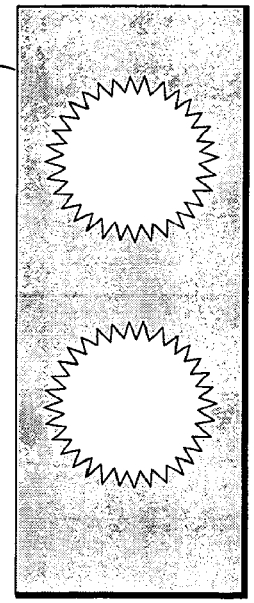

For example, with continuing reference to FIG. 8, FIG. 12 illustrates plan views of a mold 1210 of the substrate 810, a mold 1220 of the first and second disks 830, 835, and a mold 1230 of the optional second substrate 1100. Any conventional techniques and materials can be used to cast the molds 1210, 1220, 1230. For instance, die-casting or injection molding can be used to form molds 1210, 1220, 1230 comprising plastic or metal.

Figure 13:
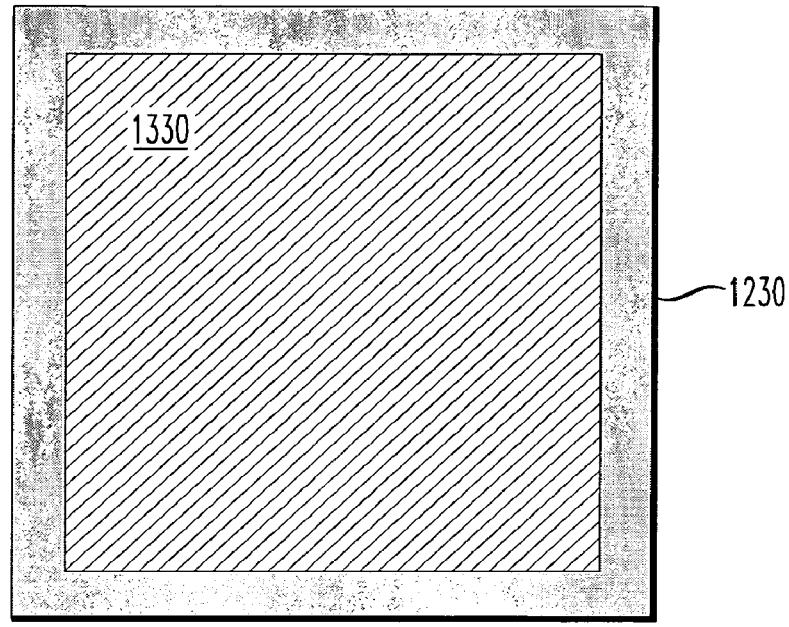
Figure 13:
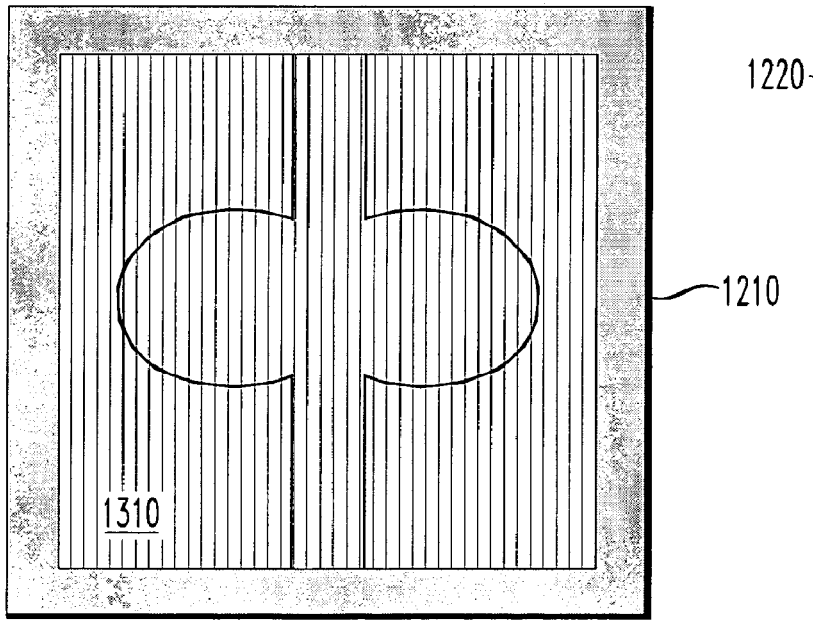
Figure 13:
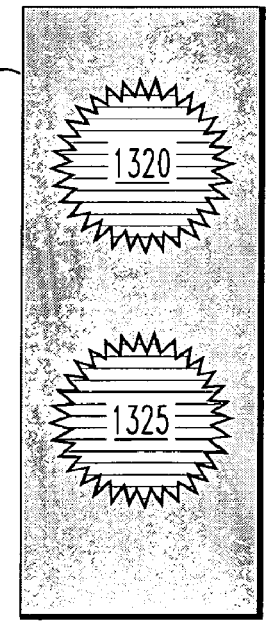

Conventional procedures are used fill the molds 1210, 1220, 1230 thereby forming replicas of components of the apparatus 800. While maintaining reference to FIG. 8, FIG. 13 illustrates a plan view of a replica 1310 of the substrate 810, replicas 1320, 1325 of the first and second disks 830, 835 and a replica 1330 of the second substrate 1100 while still in their respective molds 1210, 1220, 1230. The replicas 1310, 1320, 1325, 1330 can be composed of the same or different plastic or metal materials as the molds 1210, 1220, 1230.

Figure 14:
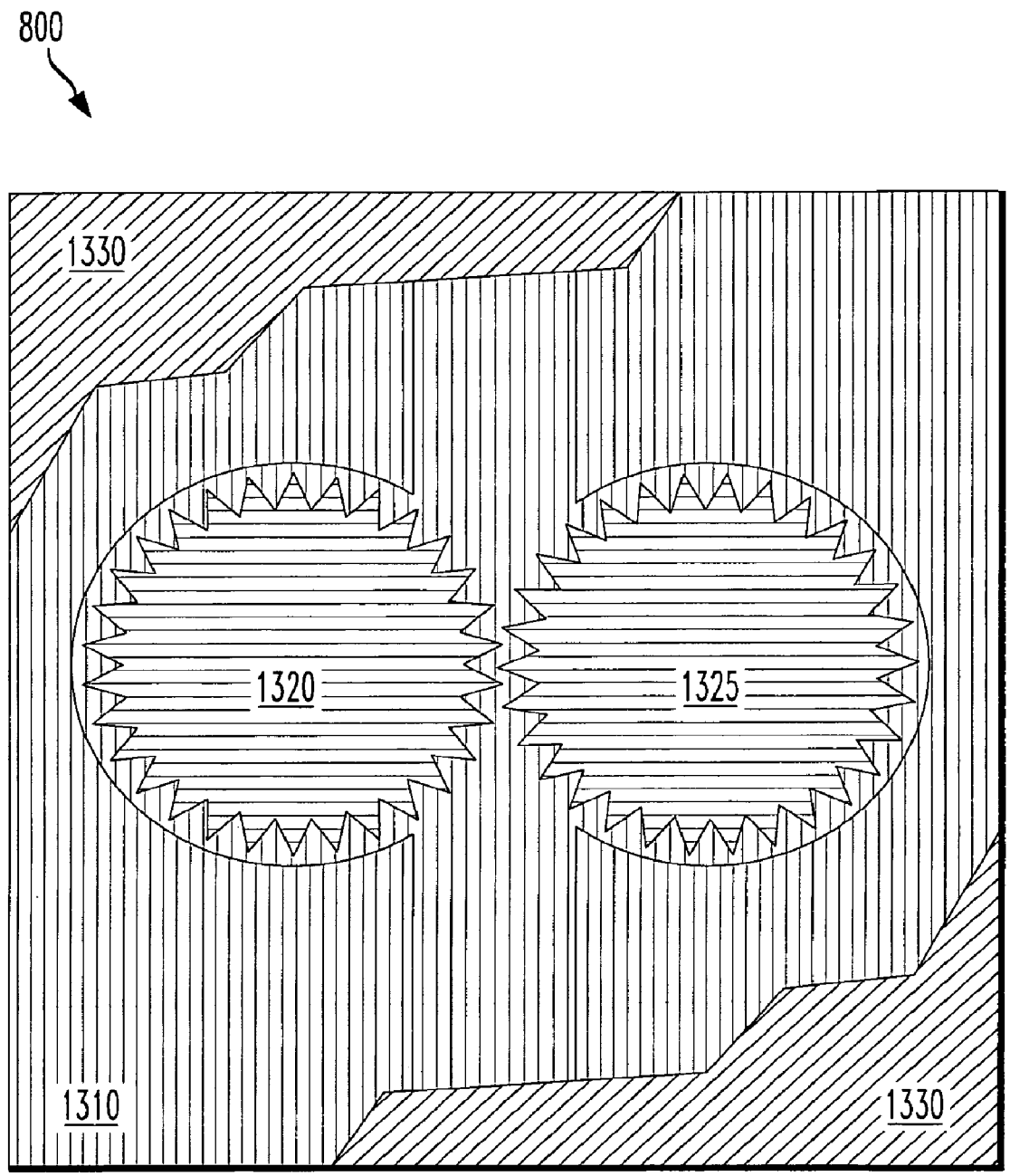

With continuing reference to FIG. 13, FIG. 14 presents a plan view of the replicas 1310, 1320, 1325, 1330 after being removed from their molds and assembled to form the apparatus 800. In some cases, the assembly of the replicas 1310, 1320, 1325, 1330 is facilitated through the use of automated micromanipulators, similar to that used in the assembly of integrated circuits. The apparatus 800 formed in this fashion can comprise any of the component structures of the apparatuses discussed above and illustrated in FIGS. 1-11.

Although the present invention has been described in detail, those of ordinary skill in the art should understand that they can make various changes, substitutions and alterations herein without departing from the scope of the invention.

What is claimed is:

1. An apparatus, comprising:
    a substrate;
    first and second disks rotatably located over the substrate, each disk having an outer circumference with teeth thereon; and
    wherein the first disk is positioned to interleave one or more of its teeth with the teeth of the second disk, the substrate includes a channel with an exit port located near the teeth of one of the disks, and a maximum distance between adjacent ones of interleaved teeth is less than about 10 microns.

2. The apparatus of claim 1, wherein the first and second disks are located in a well of the substrate, and a maximum distance between an apex of each of the teeth and a wall defining the well is less than about 10 microns.

3. The apparatus of claim 2, wherein the well is configured to hold the interleaved teeth of the disks near the exit port.

4. The apparatus of claim 2, further including a second substrate on the substrate wherein the substrate and second substrate hold the first and second disks in the well.

5. The apparatus of claim 4, wherein the substrate and second substrate are both planar.

6. The apparatus of claim 1, wherein the port is positioned to deliver fluid between the interleaved ones of the teeth.

7. The apparatus of claim 1, wherein the disks have diameters of less than about 2000 microns and the teeth have a length that is about 5 times smaller than the diameter of the disks.

8. The apparatus of claim 1, wherein the first and second disks are configured to provide the maximum distance between the adjacent ones of the interleaved teeth that is less than a diameter of a bacterium locatable there-between, wherein the diameter ranges from about 1 to about 1.5 microns.

9. The apparatus of claim 1, wherein the rotation of the first and second disks are able to cooperate to apply a mechanical force through the interleaved ones of the teeth to a microparticle locatable there-between such that the force crushes the microparticle.

10. The apparatus of claim 1, wherein the disks are positioned such that rotational motion of the disks is able to pump a fluid from the channel.

11. The apparatus of claim 1, wherein the disks are positioned such that the movement of fluid through the channel is able to cause rotational motion of the disks.

12. The apparatus of claim 1, further comprises a continuous flow system, wherein a flow of a liquid through the channel causes rotational motion of the disks.

13. The apparatus of claim 1, wherein a length of the teeth is less than about 10 microns.

14. The apparatus of claim 1, wherein the teeth have a triangular or pyramidal shape.

15. The apparatus of claim 1, wherein apexes of the teeth have angular widths of about 90 degrees or less.

16. The apparatus of claim 1, wherein a distance between the exit port and the outer circular circumference is less than about 1000 microns.

17. The apparatus of claim 1, wherein apexes of the teeth have angular widths of less than about 45 degrees.

18. The apparatus of claim 1, wherein the substrate and the teeth are both made of a semiconductor material.

* * * * *